United States Patent [19]

King

[11] Patent Number: 4,678,804
[45] Date of Patent: Jul. 7, 1987

[54] FUNGICIDAL BENZYLTHIOSTANNANES

[75] Inventor: William F. King, Novato, Calif.

[73] Assignee: Chevron Research Company, San Francisco, Calif.

[21] Appl. No.: 783,300

[22] Filed: Oct. 2, 1985

[51] Int. Cl.$^4$ ............ C07F 7/22; A01N 55/04; A61K 31/32
[52] U.S. Cl. ........................ 514/493; 556/88
[58] Field of Search .................. 556/88; 514/493

[56] References Cited

U.S. PATENT DOCUMENTS

| | | | |
|---|---|---|---|
| 2,789,104 | 4/1957 | Ramsden et al. | 556/88 X |
| 3,499,086 | 3/1970 | Brueckner et al. | 514/493 X |
| 3,677,738 | 7/1972 | Minieri | 514/493 X |
| 3,790,611 | 2/1974 | Gitlitz et al. | 556/88 X |
| 3,795,741 | 3/1974 | Minieri | 514/493 |
| 3,861,949 | 1/1975 | Onozuka et al. | 556/88 X |
| 3,906,103 | 9/1975 | Kushlefsky et al. | 514/493 |
| 4,222,950 | 9/1980 | Gitlitz | 556/88 |
| 4,301,173 | 11/1981 | Imazaki et al. | 556/88 X |
| 4,560,702 | 12/1985 | Ploss | 514/493 |

OTHER PUBLICATIONS

Chemical Abstracts 67 116949d (1967).
Chemical Abstracts 79 126584t (1973).

*Primary Examiner*—Helen M. S. Sneed
*Attorney, Agent, or Firm*—S. R. LaPaglia; R. C. Gaffney; S. L. Biggs

[57] ABSTRACT

Compounds of the formula:

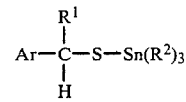

wherein Ar is aryl of 6 to 10 carbon atoms or substituted aryl of 6 to 10 carbon atoms substituted with 1 to 3 substituents selected from lower alkyl of 1 to 4 carbon atoms, halogen, trihalomethyl, and nitro; $R^1$ is hydrogen or lower alkyl of 1 to 3 carbon atoms; and $R^2$ is lower alkyl of 1 to 6 carbon atoms, lower cycloalkyl of 3 to 8 carbon atoms, aralkyl of 7 to 11 carbon atoms or aryl of 6 to 10 carbon atoms. The present invention is also directed to the associated compositions and methods of use comprising those compounds, which are fungicidal and in some cases insecticidal.

17 Claims, No Drawings

FUNGICIDAL BENZYLTHIOSTANNANES

BACKROUND OF THE INVENTION

The present invention relates to novel benzylthiostannanes which are active as fungicides. These compounds are useful in protecting plants against a variety of fungal pests.

Certain organotin derivatives have been shown to be fungicidal and, in some cases, acaricidal.

My commonly assigned U.S. patent application Ser. Nos. 655,485 and 693,908 disclose 2-pyridylthio tin N-oxides which are fungicidal and acaricidal.

U.S. Pat. No. 3,499,086 discloses methods and compositions for controlling fungal and bacterial infestations of plants which use an organic tetravalent tin compound of the formula:

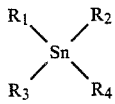

wherein $R_1$, $R_2$, $R_3$, and $R_4$ represent the same or different alkyl, aryl, aralkyl, haloalkyl and cyclo aliphatic radicals, any of which may be replaced up to a maximum of 3 by halogens, aliphatic and aromatic mono- and dicarboxylic acid radicals, radicals of mono- and polyvalent alcohols, either alcohols, phenols and thiophenols, or halogen and nitro derivatives thereof. It has been found that compounds in which at least two of the four R-positions in the formula are filled in by the normal or secondary butyl radicals are especially recommendable for such purposes.

U.S. Pat. No. 3,906,103 discloses novel tricyclohexyltin compounds of the formula:

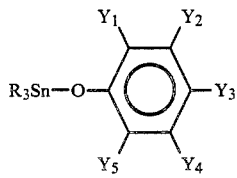

wherein R is cyclohexyl and $Y_{1-5}$ are the same or different and Y is selected from the group consisting of alkyl, aryl, cycloalkyl, halogen, nitro, mercapto, cyano, and hydrogen, such that not more than four Y substituents are hydrogen.

SUMMARY OF THE INVENTION

The present invention is directed to fungicidal compounds of the formula:

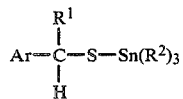

wherein Ar is aryl of 6 to 10 carbon atoms or substituted aryl of 6 to 10 carbon atoms substituted with 1 to 3 substituents selected from lower alkyl of 1 to 4 carbon atoms, halogen, trihalomethyl, and nitro; $R^1$ is hydrogen or lower alkyl of 1 to 3 carbon atoms; and $R^2$ is lower alkyl of 1 to 6 carbon atoms, lower cycloalkyl of 3 to 8 carbon atoms, aralkyl of 7 to 11 carbon atoms or aryl of 6 to 10 carbon atoms. The present invention is also directed to the associated fungicidal compositions and methods of use comprising those compounds.

Among other factors, the present invention is based upon my finding that these compounds are surprisingly active as fungicides and are effective in controlling certain plant fungal diseases. In particular, these compounds are useful in controlling plant fungal diseases such as those caused by *Piricularia oryzae, Septoria apii,* and *Erysiphe polygoni.*

In addition, certain of these compounds are acaricidal, being active as miticides and as mite ovicides. Also, some of these compounds show bactericidal activity and herbicidal activity, primarily in post-emergent applications.

Preferred Ar groups include phenyl or phenyl substituted with 1 to 3 substituents independently selected from halogen, methyl, trifluoromethyl, or nitro. Especially preferred are compounds where Ar is mono- or dihalophenyl, tolyl or dimethylphenyl.

Preferred $R^1$ groups include hydrogen or methyl.

Preferred $R^2$ groups include phenyl and cyclohexyl.

Definitions

As used herein, the following terms have the following meanings unless expressly stated to the contrary.

The term "alkyl" refers to both straight- and branched-chain alkyl groups. The term "lower alkyl" refers to both straight- and branched-chain alkyl groups having a total of from 1 to 6 carbon atoms and includes primary, secondary and tertiary alkyl groups. Typical lower alkyls include, for example, methyl, ethyl, n-propyl, isopropyl, n-butyl, isobutyl, t-butyl, n-pentyl, n-hexyl, and the like.

The term "halo" or "halogen" refers to the groups fluoro, chloro, bromo and iodo.

The term "aryl" refers to aryl groups having from 6 to 10 carbon atoms and includes, for example, phenyl, p-chlorophenyl, m-methylphenyl, p-butylphenyl, m-trifluoromethylphenyl, naphthyl, and the like.

The term "aralkyl" refers to an alkyl group of from 1 to 4 carbon atoms substituted with an aryl group of from 6 to 10 carbon atoms and includes, for example, benzyl, p-chlorobenzyl, p-methyl-benzyl, 2-phenylethyl, and the like.

The term "cycloalkyl" refers to cyclic alkyl groups, both those which are unsubstituted and those which are ring-substituted with 1 or more alkyl groups. The term "lower cycloalkyl" refers to cycloalkyl groups having a total of from 3 to 8 carbon atoms and includes, for example, cyclohexyl, cyclopentyl, 1-methylcyclopropyl, and the like.

The terms "insecticide" and "insect" as used herein refer to their broad and commonly understood usage rather than to those creatures which, in the strict biological sense, are classified as insects. Thus, the term "insect" is used not only to include small invertebrate animals belonging to the class "Insecta", but also to other related classes of arthropods such as Arachnida, whose members are segmented invertebrates having more or fewer than six legs, such as spiders; mites, ticks and other acarines; centipedes; worms; and the like.

DETAILED DESCRIPTION OF THE INVENTION

The compounds of the present invention may be conveniently prepared according to the following reaction scheme:

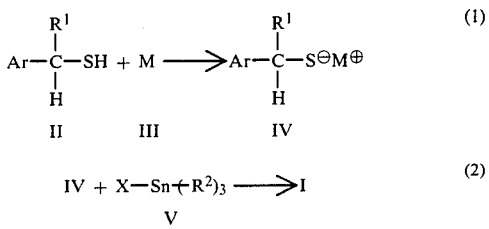

wherein Ar, $R^1$ and $R^2$ are as previously defined in conjunction with Formula I, X is halogen and M is a basically reacting metal compound which is capable of removing the proton from the thiol of II.

Reaction (1) is conducted by combining approximately equimolar amounts of II and III in solvent. Suitable solvents include protic and non-protic solvents such as methanol, ethanol, tetrahydrofuan, dimethoxyethane, and the like. The reaction is conducted at a temperature of about 0° C. to about 60° C., preferably from about 10° C. to about 30° C., or, for convenience, at room temperature, and is generally complete within about 2 to about 4 hours. The product IV is isolated by conventional procedures such as stripping, or, after removal of the solvent, may be used in Reaction (2) without further isolation and/or purification. Optionally, a strong organic base such as triethylamine may be used in place of M.

Reaction (2) is conducted by combining IV and V in solvent. Although approximately equimolar amounts of IV and V may be used, it is preferred to add an excess of IV, on the order of about 2% to about 10% excess IV per equivalent V which results in better yields of product and cleaner product. Excess IV may be conveniently removed by washing with water. Suitable solvents include organic solvents such as toluene, methylene chloride, methanol, ethanol, tetrahydrofuran, and the like. The reaction is conducted at a temperature of about 0° C. to about 110° C, preferably from about 10° C. to 40° C., or at reflux, and is generally complete within about 4 to about 8 hours. The product I is isolated by conventional procedures such as stripping, extraction, washing, filtration, and the like.

Alternatively, product I may be made directly from the corresponding thiol, II, by reacting it with V in the presence of base. In that case, the reaction is conducted at a temperature of from about 0° C. to about 80° C., preferably from about 10° C. to about 40° C., or at reflux. The reaction is generally complete within about 4 to about 8 hours. Suitable solvents include protic and non-protic solvents such as ethanol, dimethoxyethane, tetrahydrofuan, toluene, and the like. Product I may then be isolated by conventional methods as described in connection with Reaction (2).

Utility

The compositions and methods of the present invention are useful in controlling a variety of pests, including insects, acarines, certain plant fungal infections and undesired vegetation.

These compounds are active as fungicides and are particularly effective in controlling a variety of fungi which are deleterious to plants, including plant fungal infections. These compounds are particularly effective in controlling leaf spot diseases, including diseases caused by organisms such as Aspergillus, *Piricularia oryzae, Phytophthora infestans, Erysiphe polygoni* and Fusarium.

These compounds are also effective as insecticides and acaricides and may be used in controlling a variety of insect and arthropod pests. In particular, these compounds are particularly effective in controlling acarines such as mites and lepidopteraus such as cabbage leopers.

Like most insecticides and acaricides, the compounds are not usually applied full strength, but are generally incorporated with conventional biologically inert extenders or carriers normally employed for facilitating dispersion of active ingredients for agricultural chemical application, recognizing the accepted fact that the formulation and mode of application may affect the activity of a material. The toxicants of this invention may be applied as sprays, dusts, or granules to the insects, their environment or hostages susceptible to insect attack. It may be formulated as granules of large particle size, powdery dusts, wettable powders, emulsifiable concentrates, solutions, or as any of several other known types of formulations, depending on the desired mode of application.

Wettable powders are in the form of finely divided particles which disperse readily in water or other dispersants. These compositions normally contain from about 5% to 80% insecticide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the insecticidal composition.

Dusts are freely flowing admixtures of the active insecticide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the insecticide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for insecticidal applications include simple solutions of the active insecticide in a dispersant in which it is completely soluble at the desired concentration, such as acetone, alkylated naphthalenes, xylene, or other organic solvents. Granular formulations, wherein the insecticide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying insecticides are well known in the art.

The percentages by weight of the insecticide may vary according to the manner in which the composition is to be applied and the particular type of formulation, but in general comprise 0.5% to 95% of the toxicant by weight of the insecticidal composition.

The insecticidal compositions may be formulated and applied with other active ingredients, including nematocides, insecticides, fungicides, bactericides, plantgrowth regulators, fertilizers, etc. In applying the chemical, an effective amount and concentration of the toxicant of this invention is, of course, employed.

When used as a fungicide, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicide of this invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A particularly preferred embodiment for the herbicidal compositions is as a wettable powder. The wettable powder desirably contains the above-mentioned herbicidally-active compound and an inert carrier such as kaolin clay, talc, attapulgite, calcium carbonate or magnesium carbonate. Kaolin clay is an especially preferred inert carrier. Also, desirably the composition contains a surfactant or dispersing agent such as are known in the art for aiding the dispersion of the finely-divided powder ingredients of the composition in a solvent such as water. The surfactant may be of the nonionic type or the ionic type and can be selected from materials such as calcium alkyl sulfonates or sodium lauryl sulfonate, or a lignosulfonate salt.

Preferred amounts of the ingredients of the composition are 1-90% active compound, 10-95% inert carrier and 0.5-15% surfactant. More preferred ranges are 10-80% active, 20-90% inert carrier and 1-9% surfactant. Particularly preferred wettable powder herbicidal compositions of the present invention contain about 40-60% active, 40-60% inert carrier and 2-8% surfactant. Percentages in this specification are by weight unless indicated otherwise.

The herbicidal composition of the present invention may alternatively be formulated as a "flowable" with either an oil or water base. In the instance of a flowable herbicidal composition, the oil or water base is considered, for purposes of the present specification, as the inert carrier. Desirably, the flowable composition will also contain a suspending agent or thickener. Types of suspending agents known in the art include the following: density suspension, clay suspension, polymer suspension or surfactant suspension.

Preferably, the flowable herbicidal composition in accordance with the present invention contains 20–70% active, 30–80% inert carrier (oil or water base), and 1–10% suspending agent.

In the case of either the wettable powder or the flowable herbicidal composition of the present invention, preferably the active compound is micronized; that is, very finely divided into particle sizes between about 0.5 and 20 microns, more preferably between 2 and 8 microns, for purposes of formulating the final herbicidal composition.

Preferred amounts of the fungicidal, insecticidal and acaricidal compositions are from about 0.5 to about 95% by weight active compound (ingredient), from about 5 to about 99.5% inert carrier and about 0 to about 20% of a surfactant.

A further understanding of the invention can be had in the following non-limiting Examples. Wherein, unless expressly stated to the contrary, all temperature ranges refer to the Centigrade system and the term "ambient" or "room temperature" refers to about 20° C. to about 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

EXAMPLES

EXAMPLE 1

Preparation of 2,5-Dimethylbenzylthio-triphenylstannane

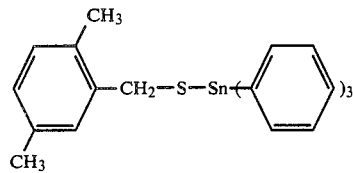

(a) To a mixture of 5.4 g (0.035 moles) of 2,5-dimethylbenzylthiol in methanol (about 50 ml) which had been stirred at room temperature for about fifteen minutes, 0.8 g (0.035 moles) sodium metal was added at one time; and the resulting mixture was stirred until all the sodium was dissolved. The methanol was removed by reduced pressure and heat to give the sodium salt which was used in Step (b) without further isolation and/or purification.

(b) Toluene (about 75 ml) was added to the salt from Step (a); the resulting mixture was stirred. To that mixture, 10 g (0.026 moles) triphenyltin chloride was added in one portion. The reaction mixture was stirred and refluxed for about 6 hours. The toluene was removed by stripping. Methylene chloride (about 150 ml) and water (about 50 ml) was added to the residue; the resulting mixture was stirred. The layers were phase separated. The organic layer was washed 3 times with (about 50 ml) water. The methylene chloride layer was dried over magnesium sulfate, then stirred with charcoal and celite and stripped to give about 9 g of the above-identified product as an opaque liquid.

Elemental analysis for $C_{27}H_{26}SSn$ showed: calculated % C 64.9, % H 5.23, and % N 0; found % C 61.48, % H 5.88, and % N 0.04.

EXAMPLE 2

Preparation of 4-Chlorobenzylthio-tricyclohexylstannane

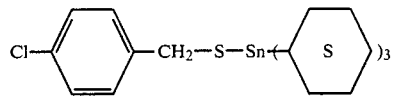

A mixture of 2.69 g (0.017 mole) 4-chlorobenzylthiol, 0.68 g (0.017 mole) sodium hydroxide in ethanol (about 75 ml) were stirred until the sodium hydroxide had dissolved. To that mixture, 6.86 g (0.017 mole) tricyclohexyltin chloride was added in one portion. The reaction mixture was refluxed. The progress of the reaction was monitored by following the pH with pH paper. When the pH of the reaction mixture became neutral, the solvent was removed by reduced pressure and a hot water bath. Water (about 50 ml) and methylene chloride (about 150 ml) were added to the residue; the resulting mixture was stirred. The layers were phase separated. The methylene chloride layer was washed three times with water and then dried over magnesium sulfate to yield about 8 g of the above-identified product as a thick opaque liquid.

Elemental analysis for $C_{25}H_{39}ClSSn$ showed: calculated % C 57.1, % H 7.48, and % N 0; found % C 57.43, % H 7.76, and % N 0.54.

EXAMPLE 3

Preparation of 2,6-Dichlorobenzylthio-triphenylstannane

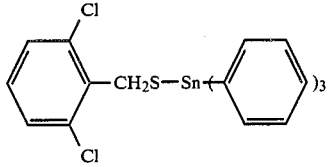

A mixture of 3.3 g (0.017 mole) 2,6-dichlorobenzylthiol, 6.86 g (0.017 moles) of 95% triphenyltin chloride, 0.7 g (0.0175 moles) sodium hydroxide, and 3 ml water in about 50 ml ethanol was stirred and refluxed for several hours. Some of the ethanol was removed by vacuum and a hot water bath. Water (about 50 ml) and methylene chloride (about 150 ml) were then added and the mixture was stirred together. The layers were phase separated. The methylene chloride layer was washed three times with water, dried over magnesium sulfate and filtered. The methylene chloride was removed by stripping to give about 8.7 g of the above-identified product as an off-white solid, melting point 88°–90° C.

Elemental analysis for $C_{25}H_{20}Cl_2SSn$ showed: calculated % C 55.4, % H 3.72, and % N 0; found % C 55.26, % H 3.86, and % N 0.18.

Compounds made in accordance with the methods disclosed in the Detailed Description of the Invention and Examples 1 to 3 are found in Table I.

In addition, by following the procedures disclosed in the Detailed Description of the Invention and in Examples 1 to 3 and using the appropriate starting materials and reagents, the following compounds are made:
2,5-dimethylbenzylthio-tricyclohexylstannane;
2,5-dimethylbenzylthio-tri-n-butylstannane;
2,5-dimethylbenzylthio-trimethylstannane;
4-methylbenzylthio-triphenylstannane;
4-methylbenzylthio-tricyclohexylstannane;
4-methylbenzylthio-tri-n-butylstannane;
4-ethylbenzylthio-triphenylstannane;
4-ethylbenzylthio-tricyclohexylstannane;
2-trifluoromethylbenzylthio-triphenylstannane;
2-trifluoromethylbenzylthio-tricyclohexylstannane;
2-trifluoromethylbenzylthio-tri-n-butylstannane;
2-trifluoromethylbenzylthio-trimethylstannane;
3-trifluoromethylbenzylthio-triphenylstannane;
3-trifluoromethylbenzylthio-tricyclohexylstannane;
4-trifluoromethylbenzylthio-triphenylstannane;
4-trifluoromethylbenzylthio-tricyclohexylstannane;
4-trifluoromethylbenzylthio-tri-n-butylstannane;
3-nitrobenzylthio-triphenylstannane;
3-nitrobenzylthio-tricyclohexylstannane;
3-nitrobenzylthio-tri-n-butylstannane;
3-nitrobenzylthio-trimethylstannane;
3,5-dinitrobenzylthio-triphenylstannane;
3,5-dinitrobenzylthio-tricyclohexylstannane;
3,5-dinitrobenzylthio-tri-n-butylstannane;
2-chlorobenzylthio-triphenylstannane;
2-chlorobenzylthio-tricyclohexylstannane;
2-chlorobenzylthio-tri-n-butylstannane;
2,4,6-trichlorobenzylthio-triphenylstannane;
2,4,6-trichlorobenzylthio-tricyclohexylstannane;
2,4,6-trichlorobenzylthio-tri-n-butylstannane;
2,4,6-trichlorobenzylthio-trimethylstannane;
2,6-dichlorobenzylthio-tricyclohexylstannane;
2,6-dichlorobenzylthio-tri-n-butylstannane;
2-bromobenzylthio-triphenylstannane;
2-bromobenzylthio-tricyclohexylstannane;
2-bromobenzylthio-tri-n-butylstannane;
4-bromobenzylthio-triphenylstannane;
4-bromobenzylthio-tricyclohexylstannane;
4-bromobenzylthio-tri-n-butylstannane;
2-fluorobenzylthio-triphenylstannane;
2-fluorobenzylthio-tricyclohexylstannane;
2-fluorobenzylthio-tri-n-butylstannane;
4-fluorobenzylthio-triphenylstannane;
4-fluorobenzylthio-tricyclohexylstannane;
4-tert-butylbenzylthio-triphenylstannane;
4-tert-butylbenzylthio-tricyclohexylstannane;
4-tert-butylbenzylthio-tri-n-butylstannane;
2-methylbenzylthio-triphenylstannane;
2-methylbenzylthio-tricyclohexylstannane;
2-methylbenzylthio-tri-n-butylstannane;
2,4,6-trimethylbenzylthio-triphenylstannane;
2,4,6-trimethylbenzylthio-tricyclohexylstannane;
2,4,6-trimethylbenzylthio-tri-n-butylstannane; and
2,4,6-trimethylbenzylthio-trimethylstannane.

EXAMPLE A

Bacterial Inhibition

Compounds of this invention were evaluated for in vitro bactericidal effectiveness by means of a bacterial inhibition test. This test is designed to measure the antibacterial activity of compounds in terms of degree of inhibition of bacterial multiplication. The representative bacteria used were *Erwinia amylovora, Pseudomonas syringae* and *Xanthomonas vesicatoria*. Each compound to be tested was dissolved in acetone to give a 500 ppm concentration. Agar plates were inoculated using a micro sprayer with an suspension of the particular bacteria shortly (3 to 5 seconds) before treatment. The inoculated agar plates were then treated with the compound to be tested by spraying with a micro sprayer. The treated plates were incubated at 23.5° C. and the data was taken 24 hours after treatment. Antibacterial activities are measured by a zone of inhibited bacterial growth from the center of the agar plate and the deposit concentration in mg/cm2 at the edge of the zone of inhibition ($ED_{99}$). The effectiveness of the compounds for antibacterial activity are reported in Table II in terms of the percent of the $ED_{99}$ of each compound of the $ED_{99}$ of the standard PMA (phenyl mercuric acetate).

EXAMPLE B

Mycelial Inhibition

Compounds were evaluated for in vitro fungicidal effectiveness by means of a mycelial inhibition test. This test is designed to measure the fungitoxic activity of fungicidal chemicals in terms of their degree of inhibition of mycelium growth. Fungi used were *Pythium ultimum, Rhizoctonia solani, Fusarium moniloforme, Botrytis cinerea, Aspergillus niger* and *Ustilago hordeii*. Each compound to be tested was dissolved in acetone to 500 ppm concentration. Paper strips were infused with the particular mycelium growth by covering the paper with a potato dextrose broth culture of mycelial suspension. The papers were then placed on potato dextrose agar plates and sprayed by means of a micro sprayer with the fungicidal solution. The treated paper strips were incubated at 25° C. and the data is taken after 24 hours. Fungicidal activities are measured by a zone of inhibited mycelial growth from the center of the paper strip in terms of mg/cm$^2$ needed for 99% control of the fungus ($ED_{99}$). The effectiveness of the compounds for fungicidal activity are reported in Table III in terms of the percent of the $ED_{99}$ of the test compound of the $ED_{99}$ of the standard Difolatan ®.

EXAMPLE C

Tomato Late Blight

Compounds were tested for the preventative control of the Tomato Late Blight organism *Phytophthora infestans*. Five- to six-week-old tomato (cultivar Bonny Best) seedlings were used. The tomato plants were sprayed with a 200-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table III.

EXAMPLE D

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 - 100 \times \left( \frac{\% \text{ disease in treated plants}}{\% \text{ disease in check}} \right)$$

The results are tabulated in Table III.

EXAMPLE E

Tomato Early Blight

Compounds were tested for the control of the Tomato Early Blight organism *Alternaria solani*. Tomato (variety Bonny Best) seedlings of 6- to 7-weeks old were used. The tomato plants were sprayed with a 200-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The results are tabulated in Table III.

EXAMPLE F

Celery Late Blight

The Celery Late Blight tests were conducted using celery (Utah) plants 11 weeks old. The Celery Late Blight organism was *Septoria apii*. The celery plants were sprayed with 200-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given test compound is based on the percent disease reduction relative to untreated check plants. The results are reported in Table III.

EXAMPLE G

Bean Powdery Mildew

Compounds were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results as percent control are tabulated in Table III.

EXAMPLE H

Bean Rust

Compounds were evaluated for their ability to eradicate Bean Rust caused by *Uromyces phaseoli typica* on pinto beans.

Pinto bean plants, variety Idaho 1-11, 16 (summer) or 19 (winter) days old were inoculated with a 50-ppm suspension of uredospores in water containing a small amount of nonionic surfactant. The inoculated plants were placed in an environmental chamber immediately after inoculation and incubated 20 hours. Following the incubation period, the plants were removed from the chamber and placed in a greenhouse maintained at 66°-68° F. and 60-80% relative humidity. Two days after inoculation, the plants were treated by spraying with a 200-ppm solution of test compound in an acetone and water carrier formulation containing a small amount of nonionic surfactant. One or two replicate pots (each containing two plants) were used for each compound. In addition one or two replicate pots were sprayed with the same carrier formulation (without a test compound) as a control (hereinafter "untreated checks"). The plants were kept in the greenhouse until evaluated. The plants were evaluated for disease control when disease symptoms were well developed on the untreated Checks, normally about 14 days after treatment. The percentage disease control (or eradication) provided by a test compound was based on the percent disease reduction relative to the untreated Checks. The results are reported in Table III.

EXAMPLE I

Aphid Control

The compounds of this invention were tested for their insecticidal activity against cotton aphids (*Aphis gossypii* Glover). An acetone solution of the test compound containing a small amount of nonionic emulsifier was diluted with water to give a concentration of 40 ppm. Cucumber leaves infested with cotton aphids were dipped in the test compound solution. Mortality readings were taken after 24 hours. The results are tabulated in Table IV in terms of percent control.

EXAMPLE J

Aphid Systemic Evaluation

This procedure is used to assess the ability of a candidate insecticide to be absorbed through the plant root system and translocate to the foliage and thus to show insecticidal activity against the cotton aphid (*Aphis gossypii* Glover).

Two cucumber plants planted in a 4-inch fiber pot with a soil surface area of 80 cm$^2$ are used. Forty ml of an 80-ppm solution of the candidate insecticide is poured around the plants in each pot. (This corresponds to 40 gamma/cm$^2$ of actual toxicant.) The plants are maintained throughout in a greenhouse at 75°-85° F. Forty-eight hours after the drenching, the treated plants are infested with aphids by placing well-colonized leaves over the treated leaves so as to allow the aphids to migrate easily from the inoculated leaf to the treated leaf. Three days after infestation, mortality readings were taken. The results are tabulated in Table IV in terms of percent control.

EXAMPLE K

Mite Adult

Compounds of this invention were tested for their insecticidal activity against parathion-resistant Two-spotted Spider Mite (*Tetranychus urticae* Koch). An acetone solution of the candidate toxicant containing a small amount of nonionic emulsifier was diluted with water to 40 ppm. Lima bean leaves which were infested with mites were dipped in the toxicant solution. The results are tabulated in Table IV in terms of percent control.

EXAMPLE L

Mite Egg Control

Compounds of this invention were tested for their ovicidal activity against eggs of the two-spotted spider mite (*Tetranychus urticae* Koch). An acetone solution of the test toxicant containing a small amount of nonionic emulsifier was diluted with water to give a concentration of 40 ppm. Two days before testing, 2-week old lima bean plants were infested with spider mites. Two days after infestation, leaves from the infested plants are dipped in the toxicant solution, placed in a petridish with filter paper and allowed to dry in the open dish at room temperature. The treated leaves were then held in covered dishes at about 31° C. to 33° C. for seven days. On the eighth day egg mortality readings are taken. The results, expressed as percent control, are tabulated in Table IV.

EXAMPLE M

Housefly

Compounds of this invention were tested for their insecticidal activity against the Housefly (*Musca domestica* Linnaeus). A 500-ppm acetone solution of the candidate toxicant was placed in a micro sprayer (atomizer). A random mixture of anesthetized male and female flies was placed in a container and 55 mg of the above-described acetone solution was sprayed on them. A lid was placed on the container. A mortality reading was made after 24 hours. The results are tabulated in Table IV in terms of percent control.

EXAMPLE N

American Cockroach

Compounds of this invention were tested for their insecticidal activity against Chlorodane-resistant American Cockroaches (*Periplaneta americana* Linnaeus). A 500-ppm acetone solution of the candidate toxicant was placed in a micro sprayer (atomizer). A random mixture of anesthetized male and female roaches was placed in a container and 55 mg of the above-described solution was sprayed on them. A lid was placed on the container. A mortality reading was made after 24 hours. The results are tabulated in Table IV in terms of percent control.

EXAMPLE O

Alfalfa Weevil

The compounds of this invention were tested for their insecticidal activity against Alfalfa Weevil [*Hypera brunneipennis* (Boheman)]. A 500-ppm acetone solution of the candidate toxicant was placed in a micro sprayer (atomizer). A random mixture of male and female weevils was placed in a container and 55 mg of the above-described acetone solution was sprayed on them. A lid was placed on the container. A mortality reading was made after 24 hours. The results are tabulated in Table IV in terms of percent control.

EXAMPLE P

Cabbage Looper Control

The compounds of this invention were tested for their insecticidal activity against Cabbage Looper [*Trichoplusia ni* (Hubner)]. An acetone solution of the candidate toxicant containing a small amount of nonionic emulsifier was diluted with water to give a concentration of 500 ppm. Excised cucumber leaves were dipped in the toxicant solution and allowed to dry. The leaves were then infested with Cabbage Looper larvae. Mortality readings were taken after 24 hours. The results are tabulated in Table IV in terms of percent control.

EXAMPLES Q AND R

The compound was respectively tested for pre-emergent and post-emergent activity against a variety of grasses and broad-leaf plants including one grain crop and one broad-leaf crop.

EXAMPLE Q

Pre-Emergent Herbicide Test

Pre-emergence herbicidal activity was determined in the following manner.

An acetone solution of the test compound was prepared by mixing 750 mg of the test compound, 220 mg of a nonionic surfactant and 25 ml of acetone. This solution was added to approximately 125 ml of water containing 156 mg of surfactant.

Seeds of the test vegetation were planted in a pot of soil and the test compound solution was sprayed uniformly onto the soil surface at a dose of 27.5 micrograms/cm$^2$. The pot was watered and placed in a greenhouse. The pot was watered intermittently and was observed for seedling emergence, health of the emerging seedlings, etc., for a 3-week period. At the end of this period the herbicidal effectiveness of the test compound was rated based on the physiological observations. A 0-to-100-scale was used, 0 representing no phytotoxicity and 100 representing complete kill. The results of these tests are summarized in Table IV, hereinbelow.

EXAMPLE R

Post-Emergent Test

The test compound was formulated in the same manner as described above for the pre-emergent test. The concentration of the test compound in this formulation was 5000 ppm. This formulation was uniformly sprayed on 2 similar pots of 24-day-old plants (approximately 15 to 25 plants per pot) at a dose of 27.5 micrograms/cm$^2$. After the plants had dried, they were placed in a greenhouse and then watered intermittently at their bases, as needed. The plants were observed periodically for phytotoxic effects and physiological and morphological responses to the treatment. After 3 weeks, the herbicidal effectiveness of the compound was rated based on these observations. A 0-to-100-scale was used, 0 representing no phytotoxicity and 100 representing complete kill. The results of these tests are summarized in Table V.

TABLE I

Compounds of the formula:
$$Ar-CH_2S-Sn(R^1)_3$$

| Compound | Ar | R¹ | Physical State | %C Calc. | %C Found | %H Calc. | %H Found | %N Calc. | %N Found |
|---|---|---|---|---|---|---|---|---|---|
| 1  46204 | 4-Cl-C₆H₄- | C₆H₅- | white solid | 59.2 | 57.4 | 4.17 | 4.25 | 0 | 0.42 |
| 2  46256 | 4-Cl-C₆H₄- | thienyl (C₄H₃S-) | thick, opaque | 57.1 | 57.4 | 7.48 | 7.76 | 0 | 0.54 |
| 3  46156 | 2,6-Cl₂-C₆H₃- | C₆H₅- | off-white solid, mp 88-90° C. | 55.4 | 55.3 | 3.72 | 3.86 | 0 | 0.18 |
| 4  44748 | 2,4-(CH₃)₂-C₆H₃- | C₆H₅- | opaque liquid | 64.9 | 61.5 | 5.23 | 5.88 | 0 | 0.04 |

TABLE II

Bacterial Inhibition

| Compound | Pseudo. | Erwin. | Xanth. |
|---|---|---|---|
| 1  46204 | 0 | 0 | 100 |
| 2  46256 | 0 | 0 | 0 |
| 3  46156 | 0 | 0 | 100 |
| 4  44748 | 0 | 0 | 63 |

Pseudo. = *Pseudomonas syringae*
Erwin. = *Erwinia amylovora*
Xanth. = *Xanthomonas vesicatoria*

TABLE III

Fungicidal Activity
Mycelial Inhibition

| Compound | Pyth. | Rhiz. | Fusar. | Botry. | Asper. | Ustil. | TLB | RB | TEB | CLB | BPM | BR |
|---|---|---|---|---|---|---|---|---|---|---|---|---|
| 1  46204 | 15 | 38 | 0 | 22 | 62 | 0 | 0 | 63 | 0 | 100 | 100 | 0 |
| 2  46256 | 0 | 0 | 0 | 0 | 118 | 13 | 90 | 58 | 0 | 97 | 100 | 0 |
| 3  46156 | 18 | 0 | 0 | 0 | 0 | 0 | 78 | 38 | 0 | 98 | 100 | 0 |
| 4  44748 | 30 | 21 | 112 | 28 | 180 | 14 | 96 | 94 | — | 100 | 100 | 0 |

Pyth. = *Pythium ultimum*
Rhiz. = *Rhizoctonia solani*
Fusar. = *Fusarium moniloforme*
Botry. = *Botrytis cinerea*
Asper. = *Aspergillus niger*
Ustil. = *Ustilago hordeii*
GDM = Grape Down Mildew
TLB = Tomato Late Blight
RB = Rice Blast
TEB = Tomato Early Blight
CLB = Celery Late Blight
BPM = Bean Powdery Mildew
BR = Bean Rust
— = Not Tested or Test Failed

TABLE IV

Insecticidal Activity

| Compound | AR | AW | HF | MA | ME | Aph. | AS | CL | 5-CL |
|---|---|---|---|---|---|---|---|---|---|
| 1  46204 | 0 | — | 0 | 95 | 50 | 0 | 0 | 100 | 100 |
| 2  46256 | 0 | — | 0 | 100 | 100 | 30 | 0 | 100 | 100 |
| 3  46156 | 0 | — | 0 | 0 | 80 | 0 | — | 0 | 100 |
| 4  44748 | 0 | — | 0 | 0 | 0 | 0 | 0 | 60 | 100 |

AR = American Cockroach
AW = Alfalfa Weevil
HF = Housefly
MA = Mite Adult
ME = Mite Egg
Aph. = Aphid
AS = Aphid Systemic
CL = Cabbage Looper
5-CL = 5-Day Reading of Cabbage Looper Mortality
— = Not Tested or Test Failed

TABLE V

| | Herbicidal Activity | | | | | | | | | | | | | | | |
|---|---|---|---|---|---|---|---|---|---|---|---|---|---|---|---|---|
| | Pre-Emergence | | | | | | | | Post-Emergence | | | | | | | |
| Compound | LQ | MUS | PGW | BG | CG | WO | SB | R | LQ | MUS | PGW | BG | CG | WO | SB | R |
| 1 46204 | 0 | 0 | 0 | 0 | 0 | 0 | 0 | 0 | 90 | 100 | 80 | 0 | 0 | 0 | 70 | 0 |
| 2 46256 | 0 | 0 | 0 | 0 | 0 | 0 | 0 | 0 | 20 | 45 | 25 | 0 | 0 | 0 | 35 | 0 |
| 3 46156 | 0 | 0 | 0 | 0 | 0 | 0 | 0 | 0 | 70 | 80 | 15 | 0 | 0 | 0 | 35 | 0 |
| 4 44748 | 0 | 0 | 0 | 0 | 0 | 0 | 0 | 0 | 45 | 90 | 90 | 0 | 0 | 0 | 55 | 0 |

LQ = Lambsquarter
MUS = Mustard
PGW = Pigweed
BC = Barnyard Grass
CG = Crabgrass
WO = Wild Oat
SB = Soybean
R = Rice

What is claimed is:

1. compound of the formula:

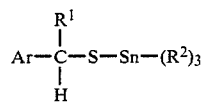

wherein Ar is monohalophenyl, dihalophenyl, tolyl or dimethylphenyl; $R^1$ is hydrogen or lower alkyl of 1 to 3 carbon atoms; $R^2$ is lower alkyl of 1 to 6 carbon atoms, lower cycloalkyl of 3 to 8 carbon atoms, aralkyl of 7 to 11 carbon atoms or aryl of 6 to 10 carbon atoms.

2. A compound according to claim 1 wherein Ar is phenyl or phenyl substituted with 1 to 3 substitutents independently selected from halogen, methyl, trifluoromethyl, or nitro.

3. A compound according to claim 1 wherein $R^1$ is hydrogen or methyl.

4. A compound according to claim 3 wherein $R^2$ is phenyl or cyclohexyl.

5. A compound according to claim 4 wherein $R^1$ is hydrogen.

6. A compound according to claim 5 wherein Ar is 2,5-dimethylphenyl.

7. A compound according to claim 6 wherein $R^2$ is phenyl.

8. A compound according to claim 6 wherein $R^2$ is cyclohexyl.

9. A compound according to claim 5 wherein Ar is 4-chloro.

10. A compound according to claim 9 wherein $R^2$ is cyclohexyl.

11. A compound according to claim 1 wherein $R^1$ is hydrogen.

12. A fungicidal composition which comprises an inert carrier and a fungicidally effective amount of a compound of claim 1.

13. A fungicidal composition which comprises an inert carrier and a fungicidally effective amount of a compound of claim 2.

14. A fungicidal composition which comprises an inert carrier and a fungicidally effective amount of a compound of claim 5.

15. A fungicidal composition which comprises an inert carrier and a fungicidally effective amount of a compound of claim 7.

16. A fungicidal composition which comprises an inert carrier and a fungicidally effective amount of a compound of claim 11.

17. A fungicidal composition which comprises an inert carrier and a fungicidally effective amount of a compound of claim 10.

* * * * *